(12) United States Patent
Ooya et al.

(10) Patent No.: US 8,980,323 B2
(45) Date of Patent: Mar. 17, 2015

(54) HYDROPHILIC MATRIX CONTAINING POORLY WATER-SOLUBLE COMPOUND AND METHOD FOR PRODUCING THE SAME

(75) Inventors: Shouji Ooya, Kanagawa (JP); Satoru Toda, Kanagawa (JP); Tetsuo Hiratou, Kanagawa (JP); Kentarou Nakamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 718 days.

(21) Appl. No.: 12/439,252

(22) PCT Filed: Aug. 29, 2007

(86) PCT No.: PCT/JP2007/066779
§ 371 (c)(1),
(2), (4) Date: Feb. 27, 2009

(87) PCT Pub. No.: WO2008/026644
PCT Pub. Date: Mar. 6, 2008

(65) Prior Publication Data
US 2010/0003323 A1    Jan. 7, 2010

(30) Foreign Application Priority Data

Aug. 29, 2006  (JP) .................................. 2006-231480

(51) Int. Cl.
*A61K 9/00*      (2006.01)
*A61K 9/70*      (2006.01)
*A61K 31/337*    (2006.01)
*A61K 31/436*    (2006.01)

(52) U.S. Cl.
CPC ............ *A61K 9/0014* (2013.01); *A61K 9/7007* (2013.01); *A61K 31/337* (2013.01); *A61K 31/436* (2013.01)
USPC ........................................................ 424/484

(58) Field of Classification Search
None
See application file for complete search history.

(56) References Cited

U.S. PATENT DOCUMENTS

| | | | |
|---|---|---|---|
| 6,737,072 B1 * | 5/2004 | Angele et al. ................. | 424/426 |
| 2001/0051131 A1 | 12/2001 | Unger | |
| 2003/0113359 A1 | 6/2003 | Iyer et al. | |
| 2003/0219853 A1 * | 11/2003 | Chou .......................... | 435/68.1 |
| 2004/0126400 A1 | 7/2004 | Iversen | |
| 2004/0224023 A1 * | 11/2004 | Hunter et al. ................. | 424/486 |

FOREIGN PATENT DOCUMENTS

| | | |
|---|---|---|
| DE | 198 55 890 A1 | 6/2000 |
| EP | 1 508 331 A1 | 2/2005 |
| EP | 2 093 248 A1 | 8/2009 |
| EP | 2 100 914 A1 | 9/2009 |
| JP | 2002-531182 A | 9/2002 |
| JP | 2003-534234 A | 11/2003 |
| JP | 2003-342168 A | 12/2003 |
| JP | 2004-523484 A | 8/2004 |
| JP | 2004-532802 A | 10/2004 |
| WO | 00/32551 A1 | 6/2000 |
| WO | 00/71079 A2 | 11/2000 |
| WO | 00/71079 A3 | 11/2000 |
| WO | 02/32397 A2 | 4/2002 |
| WO | 02/40242 A1 | 5/2002 |
| WO | 2005/012606 A2 | 2/2005 |
| WO | 2005/046521 A1 | 5/2005 |
| WO | 2007/066781 A1 | 6/2007 |

OTHER PUBLICATIONS

Lavasanifar, A. et al. "Micelles Self-Assembled From Poly(Ethylene Oxide)-Blockpoly(N-Hexyl Stearate L-Aspartamide) by a Solvent Evaporation Method: Effect on the Solubilization and Haemolytic Activity of Amphotericin B." Journal of Contorolled Release, (2001) 77 (1-2) p. 155-160.
Office Action dated Aug. 28, 2012 in Japanese Application No. JP 2008-532094.
Extended European Search Report dated Feb. 18, 2013 in European Application No. 07806256.9.
Office Action dated Oct. 16, 2013 in European Application No. 07 806 256.9.

* cited by examiner

*Primary Examiner* — Brian Gulledge
(74) *Attorney, Agent, or Firm* — Sughrue Mion, PLLC

(57) ABSTRACT

It is an object of the present invention to solve the problem of precipitation of a poorly water-soluble compound in a hydrophilic matrix upon inclusion of the poorly water-soluble compound in the hydrophilic matrix. The present invention provides a composition wherein a poorly water-soluble compound is contained in a hydrophilic matrix in a finely-dispersed state.

19 Claims, 1 Drawing Sheet

[Fig.1]
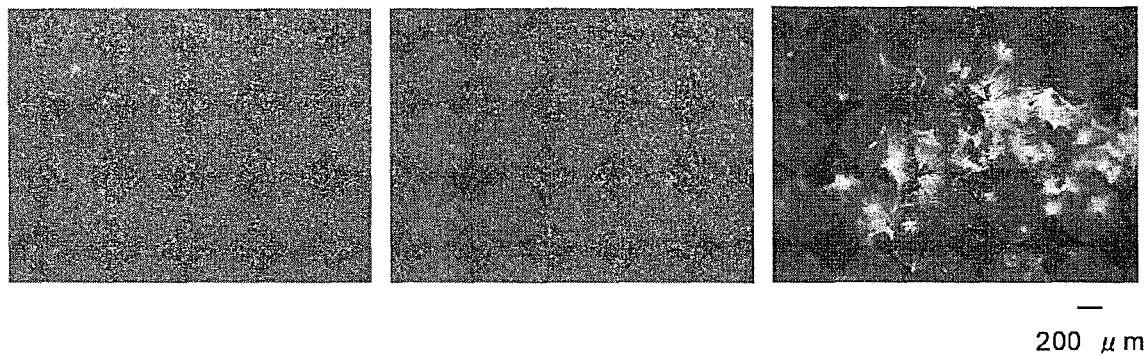
200 μm
[Fig.2]
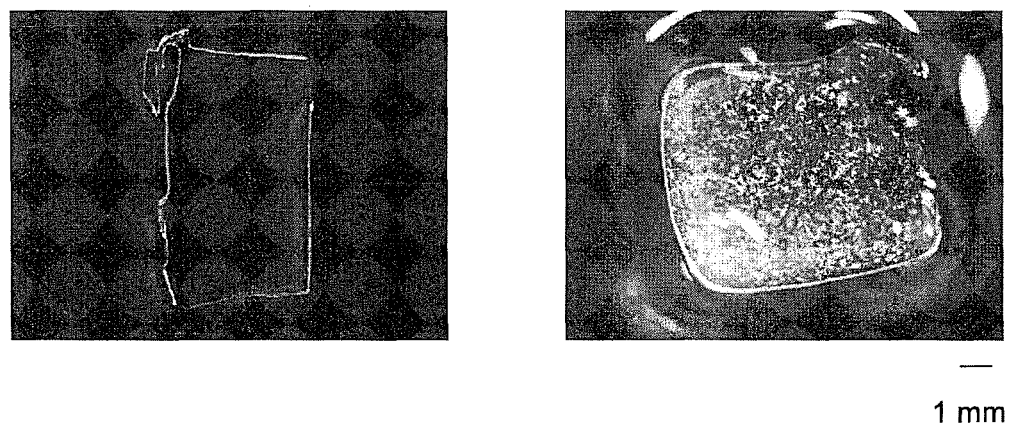
1 mm

HYDROPHILIC MATRIX CONTAINING POORLY WATER-SOLUBLE COMPOUND AND METHOD FOR PRODUCING THE SAME

TECHNICAL FIELD

The present invention relates to a hydrophilic matrix containing a poorly water-soluble compound in a finely-dispersed state at a high concentration, and a method for producing the same.

BACKGROUND ART

Many hydrophilic polymers are highly biocompatible, and thus such polymers, including biopolymers and synthetic polymers, have been widely used in the field of medicine. In particular, since biopolymers are main biological constituents, they are highly biocompatible in many cases. In addition, each biopolymer has peculiar physiological functions. Therefore, biopolymers are applied to drug delivery carriers, matrices for tissue construction, material-surface-coating materials, and the like in the field of medicine. However, many such hydrophilic polymers are water soluble. In general, a hydrophilic polymer is allowed to contain a poorly water-soluble compound by a method comprising: dissolving a hydrophilic polymer and a poorly water-soluble compound in water; allowing the compound to be immersed in water contained in the hydrophilic polymer; and using the resultant directly as a substrate (matrix) or drying it before use. According to such method, when a hydrophilic matrix contains a poorly water-soluble compound at a concentration higher than that corresponding to the solubility of the poorly water-soluble compound in water, the poorly water-soluble compound is precipitated in the hydrophilic matrix. Therefore, it is difficult to allow a hydrophilic matrix to contain a poorly water-soluble compound at a high concentration. Also, in general, when a hydrophilic matrix is allowed to contain a poorly water-soluble compound, a poorly water-soluble compound is water-solubilized with the use of a surfactant. In such case, if the surfactant content is large, chemical, physical, and optical properties of such a contained compound might change. Further, in terms of in vivo use, the toxicity of a surfactant might be observed, which is problematic. Therefore, a technique for allowing a matrix to contain a poorly water-soluble compound without surfactant or with a small amount of surfactant is very important not only in the field of medicine but also in fields involving the use of poorly water-soluble compounds (e.g., pigments) in a dispersed state.

Poorly water-soluble immunosuppressive agents (e.g., sirolimus) and anticancer agents (e.g., paclitaxel) are used as drugs for drug-eluting stents (DESs) that have been significantly developed in recent years. At present, nondegradable synthetic polymers are used for a matrix capable of containing such a drug. However, inflammation caused by long-term application of such a matrix is a matter of concern, and thus a biodegradable matrix is necessary. When collagen is used for a biodegradable hydrophilic matrix, it is difficult to allow collagen to contain a drug as described above. Therefore, a collagen matrix layer and a drug layer are alternately laminated for drug coating so that a collagen matrix does not contain such a drug (Non-Patent Document 1).

1,1,1,3,3,3-hexafluoro-2-propanol (HFIP) can dissolve protein such as collagen and gelatin, and thus it is used for production of a matrix for tissue construction (Patent Document 1) and production of a fibrous matrix by electrospinning (Patent Documents 2 and 3). However, the documents mainly focus on production of a matrix itself. None of the documents describe the inclusion of a poorly soluble compound in such a matrix or the state of the drug in the matrix.

In addition, Patent Document 4 discloses, as an emulsion vehicle containing an insufficiently soluble drug, a pharmaceutical composition containing a therapeutic agent with a low solubility, at least one type of tocol, at least one type of solvent adjuvant, and at least one type of surfactant. However, the document does not describe that a poorly water-soluble compound is contained in a hydrophilic matrix in a finely-dispersed state.

Non-Patent Document 1: Journal of Controlled Release 108, 178-189, 2005
Patent Document 1: JP Patent Publication (Kohyo) No. 2002-531182 A
Patent Document 2: JP Patent Publication (Kohyo) No. 2004-532802 A
Patent Document 3: JP Patent Publication (Kokai) No. 2004-321484 A
Patent Document 4: JP Patent Publication (Kohyo) No. 2003-500368 A

DISCLOSURE OF THE INVENTION

Object to be Solved by the Invention

It is an object of the present invention to solve the problem of conventional technology regarding precipitation of a poorly water-soluble compound in a hydrophilic matrix upon inclusion of the poorly water-soluble compound in the hydrophilic matrix. Specifically, it is an object of the present invention to provide a composition wherein a poorly water-soluble compound is contained in a hydrophilic matrix in a finely-dispersed state, and the method for producing the same.

Means for Solving the Object

According to the present invention, in order to solve the above problem, a composition wherein a poorly water-soluble compound is contained in a hydrophilic matrix in a finely-dispersed state at a high concentration has been produced with the use of an organic fluorine compound as a solvent. Specifically, since various hydrophilic matrixes and a poorly water-soluble compound can be mixed with such a solvent, a film-form composition can be produced by applying and drying the resulting mixed solution.

That is, the present invention provides a composition wherein a poorly water-soluble compound is contained in a hydrophilic matrix in a finely-dispersed state.

Preferably, there is provided a composition wherein a poorly water-soluble compound is contained in a hydrophilic matrix in a finely-dispersed state, which is obtained by coating and drying a mixture obtained by dissolving a poorly water-soluble compound and a hydrophilic matrix in an organic fluorine compound.

Preferably, the composition of the present invention is a film form which is obtained by coating a mixture that is prepared by dissolving a poorly water-soluble compound and a hydrophilic matrix in an organic fluorine compound on a substrate, followed by drying.

Preferably, the hydrophilic matrix is a biopolymer.

Preferably, the hydrophilic matrix is a protein. Preferably, the protein is at least one selected from the group consisting of collagen, gelatin, albumin, casein, fibroin, fibrin, laminin, fibronectin, and vitronectin. Particularly preferably, the protein is albumin, casein, or gelatin.

Preferably, the hydrophilic matrix is crosslinked by heat or light, or with a crosslinking agent.

Preferably, the crosslinking agent is an enzyme.

Preferably, the enzyme is transglutaminase.

Preferably, the composition of the present invention is obtained by coating a mixture that is prepared by dissolving a poorly water-soluble compound and gelatin in an organic fluorine compound on a substrate, drying the resultant to form a film, and treating the obtained film with transglutaminase to crosslink gelatin.

Preferably, the organic fluorine compound is a compound having a carbon number of 2 to 8.

Particularly preferably, the organic fluorine compound is a compound having a carbon number of 2 or 3.

Preferably, the organic fluorine compound is 1,1,1-3,3,3-hexafluoro-2-propanol, 2,2,2-trifluoro ethanol, trifluoroacetic acid, or pentafluoro propionic acid.

Preferably, the poorly water-soluble compound has a log P (logarithm of 1-octanol/water partition coefficient) of 1 to 20.

Particularly preferably, the poorly water-soluble compound has a log P (logarithm of 1-octanol/water partition coefficient) of 2 to 10.

Preferably, the poorly water-soluble compound is a drug.

Preferably, the drug is an anticancer agent, an immunosuppressive agent, an antiallergic agent, an antioxidant, an antithrombotic agent, an anti-inflammatory agent, a cosmetic component, or a supplement component.

Preferably, the drug is an anticancer agent or an immunosuppressive agent.

Preferably, the drug is paclitaxel or sirolimus.

Preferably, an additive in contained in the mixture together with the poorly water-soluble compound.

Preferably, the additive is at least one selected from the group consisting of a moisturizing agent, a softening agent, and a transdermal-absorption-promoting agent.

Preferably, a surfactant is not contained as an additive in the mixture.

Preferably, the composition of the present invention is used as a transdermally absorbable agent, a topical therapeutic agent, an oral therapeutic agent, a cosmetic, a supplement, or a pigment.

In another aspect of the present invention, there is provided a method for producing the composition of the present invention which comprises a step of coating and drying a mixture that is prepared by dissolving a poorly water-soluble compound and a hydrophilic matrix in an organic fluorine compound. Preferably, the poorly water-soluble compound is a drug.

Effect of the Invention

According to the present invention, it has become possible to provide a composition comprising a poorly water-soluble compound is contained in a hydrophilic matrix in a finely-dispersed state, and a method for producing the same. In the case of the composition of the present invention, a poorly water-soluble compound is contained in a hydrophilic matrix contains in a finely-dispersed state, which is advantageous for control of the amount of such a poorly water-soluble compound (e.g., a drug) to be released, the release rate, and the drug efficacy. Further, when the composition of the present invention is used as a transdermally absorbable agent, transdermal absorption efficiency can be improved, which is also advantageous.

BEST MODE FOR CARRYING OUT THE INVENTION

In recent years, the state-of-the-art medical technology has been dramatically advanced. Specifically, novel therapeutic methods are being developed based on a fusion of conventional therapeutic methods and drug delivery technology. For example, drug-eluting stents (DESs) are being developed. After myocardial infarction or the like, stenosed blood vessels can be restored by expanding blood vessel lumens in a physical manner with balloon catheters. However, restenosis of the thus restored blood vessels occurs. Blood vessel restenosis is prevented by placing a stent inside a blood vessel. However, even with the use of such technique, restenosis occurs at a constant rate. Blood vessel restenosis is mainly caused by intimal thickening with blood vessel smooth muscle cells (SMCs) in damaged legions. In order to inhibit intimal thickening with SMCs, a DES obtained by applying an immunosuppressive agent or an anticancer agent to the outer surface of a stent has been developed. At present, a nondegradable synthetic polymer is used as a matrix for drug inclusion for a drug-eluting stent. Therefore, problems caused by inflammation and the like as a result of long-term application of such matrix have been pointed out. It is necessary to develop a matrix capable of containing a drug, releasing the drug, and then being degraded/absorbed in vivo. However, biopolymers such as collagen that have been attempted to be used for a matrix are hydrophilic, and it is difficult for such a polymer to contain a poorly water-soluble drug. Hence, in order to use, for example, collagen for a matrix used for coating, a technique for coating a drug and a collagen matrix to prepare a layered product (Journal of Controlled Release 108, 178-189, 2005) has been carried out. In this method, it cannot be said that a drug is dissolved or exists in a finely-dispersed state in a matrix. A condition in which a drug is dissolved or exists in a finely-dispersed state in a matrix is advantageous for control of the amount of the drug to be released, the release rate, and the drug efficacy, as compared with a condition in which a drug is in a precipitated state. Further, when a drug is used as a transdermally absorbable agent, the drug is transferred from a matrix to the skin and permeates through the skin. In such case, if the drug exists in a finely-dispersed state, the transdermal absorption efficiency can be improved. Therefore, a technique for allowing a matrix used for drug inclusion to contain a drug in a dissolved state or in a finely-dispersed state is necessary.

The term "in a finely-dispersed state" used herein refers to a condition in which the contained poorly water-soluble drug, which is a compound of a size that cannot be detected with a stereo microscope (MZ16A produced by Leica), is uniformly dispersed in a matrix, or a condition in which such a drug is in a molecular dispersion state in a matrix. More specifically, the term refers to a condition in which it is observed with a scanning electron microscope (SEM) that a compound contained in a matrix has a particle size of 0.001 µm to 10 µm and is uniformly dispersed therein. The particle size of such compound is preferably 0.01 µm to 2 µm and most preferably 0.01 µm to 0.5 µm.

According to the method developed by the present invention, it is possible to use a biodegradable biopolymer for a hydrophilic matrix used for coating. It is also possible to allow the hydrophilic matrix to contain a drug at a high concentration. Accordingly, the hydrophilic matrix can be expected to be degraded after releasing a drug over a certain period of time. In addition, since such drug is poorly water-soluble in many cases, it is difficult to allow a hydrophilic matrix to contain such drug. However, the method of the present invention can be expected to be applied to a drug-eluting stent containing a drug such as an immunosuppressive agent or an anticancer agent.

The composition wherein a poorly water-soluble compound is contained in a hydrophilic matrix, that was produced by the above method, may be subjected to crosslinking according to need. When the degree of crosslinking of a hydrophilic matrix is controlled, it becomes possible to determine properties of the matrix in terms of biodegradability, strength, structure, and the like depending on application. The crosslinking method is not particularly limited. Examples of such crosslinking method include physical crosslinking, chemical crosslinking, heat crosslinking, and enzymatic crosslinking. Preferably, chemical or enzymatic crosslinking is carried out. Examples of chemical crosslinking agents include widely-used general crosslinking agents which include aldehydes such as glutaraldehyde and formaldehyde; carbodiimide; cyanamide; vinyl sulfone; diepoxide; and a crosslinking agent containing photodimerizable groups such as cinnamyl, vinyl, and coumarin. More preferably, glutaraldehyde or transglutaminase is used. Most preferably, enzymatic crosslinking with transglutaminase is carried out.

An organic fluorine compound used for the above method is not particularly limited. However, it is necessary that such a compound can be used for dissolution or suspension of a hydrophilic matrix and a poorly water-soluble compound. Preferably, such compound is in a liquid form at ordinary temperatures. Further, it is preferable to use a solvent that can be distilled away from a solution or suspension containing a poorly water-soluble compound and a hydrophilic matrix when the solution is coated. Preferred examples of such solvent include nonaromatic organic fluorine compounds having carbon numbers of 2 to 8 and aromatic fluorine-containing esters, carboxylic acids, and nitrites having carbon numbers of 6 to 12. Preferable examples of nonaromatic organic fluorine compounds having carbon numbers of 2 to 8 include fluorine-containing alcohols, fluorine-containing amides, fluorine-containing esters, fluorine-containing carboxylic acids, and fluorine-containing ethers, having carbon numbers of 2 to 8. Such a compound may be partially substituted with a non-fluorine halogen atom. A more preferable example of the compound is fluorine-containing alcohol having a carbon number of 2 to 3. The most preferable examples thereof include 1,1,1-3,3,3-hexafluoro-2-propanol, 2,2,2-trifluoro ethanol, trifluoroacetic acid, and pentafluoro propionic acid. In addition, the above solvents are compatible with a variety of solvents. Therefore, they can be used in the form of a mixed solvent with a compatible solvent.

Components of the above hydrophilic matrix are not limited as long as the matrix can be dissolved in a fluorine-containing solvent. Such components can be biopolymers, synthetic polymers, lipids, and the like. Further, a biologically derived biopolymer may be a sugar, a protein, or a precursor of either thereof. However, for example, a protein in a spherical form or a fibrous form is preferable. Preferably, collagen, gelatin, albumin, casein, fibroin, fibrin, laminin, fibronectin, or vitronectin is used. More preferably, collagen, gelatin, albumin, casein, fibroin, or laminin is used. Further preferably, collagen, gelatin, albumin, or casein is used. Among the above, albumin, casein, and gelatin are most preferable. Furthermore, the protein origin is not particularly limited. Any bovine-, pig-, or fish-derived proteins or gene recombinants thereof can be used. An example of a gene recombinant that can be used is one described in EP0926543B, WO2004-085473, EP1398324A, EP1014176A, U.S. Pat. No. 6,645,712, or the like.

The poorly water-soluble compound of the present invention can be any compound such as a pigment or drug as long as it is poorly water-soluble. In general, as an index for hydrophilicity/hydrophobicity of a compound, the Log P representing the logarithm of the partition coefficient of 1-octanol/water (pH 7.4; buffer solution) obtained by the flask-shaking method has been widely used. However, instead of obtaining such a measurement value, a value obtained by calculation can be used ("Log P" used herein is calculated with the CLOGP program (including the Hansch-Leo fragment method) built into a system (PCModels) provided by Daylight Chemical Information Systems). It has been reported that a hydrophilic compound with a negative Log P value can be readily contained in a hydrophilic matrix. However, it has been known that it is difficult to allow a poorly water-soluble compound (i.e., a compound with a Log P of 1 or more) to be uniformly contained in a hydrophilic matrix. The poorly water-soluble compound to be contained in a hydrophilic matrix in the present invention has a Log P of preferably 1 to 20, further preferably 1 to 15, particularly preferably 2 to 10, and most preferably 3 to 5.

A compound used as the poorly water-soluble compound to be contained in a hydrophilic matrix in the present invention has a solubility in 1,1,1-3,3,3-hexafluoro-2-propanol of preferably 50 mg/ml to 1000 mg/ml and further preferably 100 mg/ml to 500 mg/ml. Such compound can be maintained in a finely-dispersed state as defined in the present invention even when contained at a high concentration. The solubility in hexafluoroisopropanol is determined as described below according to the present invention. A mixture is prepared by adding a compound to 1,1,1-3,3,3-hexafluoro-2-propanol while changing the concentration of the compound in a stepwise manner, and the concentration at which precipitation takes place is examined. Thus, the solubility of the compound in 1,1,1-3,3,3-hexafluoro-2-propanol is determined. In addition, a soluble/insoluble state is determined by confirming the presence of a deposit after centrifugation of the above mixture with a micro centrifuge (Chibitan II XX42CF00T produced by Tech-Jam) for 20 seconds.

The drug is a physiologically active ingredient. Specific examples of a drug include transdermally absorbable agents, topical therapeutic agents, oral therapeutic agents, cosmetic components, and supplement components. Specifically, preferable examples of a drug that can be used include immunosuppressive agents (e.g., sirolimus, rapamycin, tacrolimus, and cyclosporine), anticancer agents (e.g., paclitaxel, Topotecin, taxotere, docetaxel, enocitabine, and 17-AAG), antipyretic analgesics (e.g., aspirin, acetaminophen, and sulpyrine), antiepileptic agents (e.g., phenyloin, acetazolamide, carbamazepine, clonazepam, diazepam, and nitrazepam), antiphlogistic analgetics (e.g., alclofenac, alminoprofen, ibuprofen, indomethacin, epirizole, oxaprozin, ketoprofen, diclofenac sodium, diflunisal, naproxen, piroxicam, Fenbufen, flufenamic acid, flurbiprofen, floctafenine, pentazocine, metiazinic acid, mefenamic acid, and mofezolac), fat-soluble vitamins (e.g., vitamin A, vitamin D2, vitamin D3, vitamin E, and vitamin K2), synthetic antibacterial agents (enoxacin, ofloxacin, cinoxacin, sparfloxacin, thiamphenicol, nalidixic acid, tosufloxacin tosilate, norfloxacin, pipemidic acid trihydrate, piromidic acid, fleroxacin, and levofloxacin), antifungal agents (e.g., itraconazole, ketoconazole, fluconazole, flucytosine, miconazole, and pimaricin), antibiotics (e.g., roxithromycin, cefditoren pivoxil, cefteram pivoxil, erythromycin, clarithromycin, telithromycin, and azithromycin), antivirals (acyclovir, ganciclovir, didanosine, zidovudine, and vidarabine), hormone drugs (e.g., insulin zinc, testosterone propionate, and estradiol benzoate), cardiovascular agents (e.g., alprostadil), antithrombotic agents, gastrointestinal agents (omeprazole, lansoprazole, teprenone, metoclopramide, and sofalcone), diabetic agents (e.g., pioglitazone hydrochloride), antioxidants, antiallergic agents (clemastine fumarate, loratadine, mequitazine, zafirlukast, Pranlukast, ebastine, tazanolast, tranilast, ramatroban, and oxatomide), steroidal anti-inflammatory agents (e.g., cortisone acetate, betamethasone, prednisolone, fluticasone propionate, dexamethasone, budesonide, beclometasone propionate, triamcinolone, loteprednol, fluorometholone, difluprednate, mometasone furoate, clobetasol propionate, diflorasone diacetate, diflucortolone valerate, fluocinonide, amcinonide, halcinonide, fluocinolone acetonide, triamcinolone acetonide, flumetasone pivalate, and clobetasone butyrate), cosmetic components, sulfa drugs (e.g., salazosulfapyridine, sulfadimethoxine, sulfamethizole, sulfamethoxazole, sulfamethopyrazine, and sulfamonomethoxine), anesthetic agents (e.g., fentanyl), ulcerative colitis therapeutic agents (e.g., mesalazine), and supplement components.

The application of the compound is not particularly limited. However, it is used as a transdermally absorbable agent, a topical therapeutic agent, an oral therapeutic agent, a cosmetic, a supplement, or a pigment. Preferably, the compound is used as a transdermally absorbable agent, a topical therapeutic agent, an oral therapeutic agent, or a cosmetic. Further preferably, it is used as a transdermally absorbable agent, a topical therapeutic agent, or an oral therapeutic agent. Most preferably, it is used as a transdermally absorbable agent or a topical therapeutic agent.

In addition, it is possible to add various additives to the above poorly water-soluble compound. Examples of an additive that can be used in the present invention include moisturizing agents (e.g., agar, diglycerine, distearyldimonium hectorite, butylene glycol, polyethylene glycol, propylene glycol, sodium hyaluronate, hexylene glycol, coix seed extract, and vaseline), softening agents (e.g., glycerin and mineral oil), emollient ingredients (e.g., isopropyl isostearate, polyglyceryl isostearate, isotridecyl isononanoate, octyl isononanoate, oleic acid, glyceryl oleate, cacao butter, cholesterol, mixed fatty acid triglyceride, dioctyl succinate, sucrose acetate stearate, cyclopentasiloxane, sucrose distearate, octyl palmitate, octyl hydroxystearate, arachidyl behenate, sucrose polybehenate, polymethylsilsesquioxane, myristyl alcohol, cetyl myristate, myristyl myristate, and hexyl laurate), transdermal-absorption-promoting agents (e.g., ethanol, isopropyl myristate, citric acid, squalane, oleic acid, menthol, N-methyl-2-pyrrolidone, diethyl adipate, diisopropyl adipate, diethyl sebacate, diisopropyl sebacate, isopropyl palmitate, isopropyl oleate, octyldodecyl oleate, isostearyl alcohol, 2-octyl dodecanol, urea, vegetable oil, and animal oil), preservatives (e.g., benzoic acid, sodium benzoate, ethylparaben, potassium sorbate, sodium sorbate, sorbic acid, sodium dehydroacetate, and methylparaben), pigments (e.g., kaolin, carmine, ultramarine blue, chromic oxide, and iron oxide), aroma chemicals, and pH adjusters (e.g., sodium citrate, sodium acetate, sodium hydroxide, potassium hydroxide, and phosphoric acid). In addition, in a preferred embodiment of the present invention, the composition of the present invention does not contain a surfactant as an additive.

Next, the method for producing a composition wherein a poorly water-soluble compound is contained in a hydrophilic matrix in a finely-dispersed state which is provided by the present invention is described. The composition of the present invention can be produced by coating and drying a mixture obtained by dissolving a poorly water-soluble compound and a hydrophilic matrix in an organic fluorine compound. For example, a mixture obtained by dissolving a poorly water-soluble compound and a hydrophilic matrix in an organic fluorine compound is coated on a substrate, followed by drying. Thus, a film can be formed. The composition may be in any form as long as it can be formed into film, fibers, powder, sponge, non-woven fabric, particles, and the like. However, in a preferred embodiment of the present invention, the composition of the present invention is in a film form that can be obtained as described above. The thickness of the composition provided by the present invention can be arbitrarily changed depending on the amount of the composition coated to an area for coating, and thus it is not particularly limited as long as the effects of the present invention can be achieved. However, the thickness is generally 0.1 µm to 1 mm and preferably 1 µm to 200 µm.

The concentration of a poorly water-soluble compound in a mixture obtained by dissolving a poorly water-soluble compound and a hydrophilic matrix in an organic fluorine compound is not particularly limited as long as the effects of the present invention can be achieved. However, one characteristic of the present invention is that a poorly soluble compound can be contained in a finely-dispersed state at a high concentration. The proportion of a poorly water-soluble compound in a hydrophilic matrix (poorly water-soluble compound/hydrophilic matrix) is not particularly limited as long as the effects of the present invention can be achieved. However, the proportion is generally 0.001% to 50%, preferably 0.01% to 10%, and most preferably 0.1% to 5%.

According to the present invention, the above mixture is coated on, for example, a polypropylene dish, a glass plate, a teflon plate, or a stainless-steel plate, followed by drying. Thus, a composition wherein a poorly water-soluble compound is contained in a hydrophilic matrix in a finely-dispersed state can be produced. Drying conditions are not particularly limited as long as the effects of the present invention can be achieved. For example, in the case of still standing, drying can be carried out at an ordinary temperature to 50° C. for 1 to 48 hours and preferably 2 to 15 hours. In some cases, vacuum drying and/or washing with water is carried out and then drying can be carried out.

Preferably, in the case of the composition produced by the method of the present invention, the amount of a solvent (used for the production) remaining in the composition is as small as possible. The solvent content in the composition is preferably 0% to 0.1%. However, in general, a minute amount of a solvent remains in the composition. Therefore, such content is most preferably 0.00001% to 0.1%. The remaining solvent content can be quantified with GC-MS following decomposition of the composition.

The present invention is hereafter described in greater detail with reference to the following examples, although the technical scope of the present invention is not limited thereto.

EXAMPLES

Example 1

Production of Paclitaxel-Containing Gelatin Gel

Paclitaxel (produced by LCL laboratories) was used as a poorly water-soluble compound. Paclitaxel has a log P of 4.7 and a solubility in HFIP of 200 to 500 mg/ml. 1,1,1,3,3,3-hexafluoro-2-propanol solution (HFIP; 200 µL) containing paclitaxel (1 mg/mL) and gelatin (100 mg/mL; PSK gelatin produced by Nippi Inc.) was coated on a polypropylene dish (2 cm×2 cm×500 µm), followed by drying at an ordinary temperature for 15 hours. Thus, a paclitaxel-containing gelatin film was produced.

Example 2

Stereo-Microscopic Observation of Paclitaxel-Containing Film and Gel

The paclitaxel-containing gelatin film produced in Example 1 was observed with a stereo microscope (produced by Leica, MZ16A). No precipitation of paclitaxel was observed in the paclitaxel-containing gelatin film produced with HFIP as in the case of a paclitaxel-free gelatin film (FIG. 1, left and center). Upon observation with a stereo microscope (produced by Leica, MZ16A), precipitation of paclitaxel was not observed. Therefore, the size of paclitaxel in the paclitaxel-containing gelatin film produced with HFIP was found to be 10 μm or less. Meanwhile, in the case of a film produced with water-ethanol, a precipitate having a size of approximately several hundreds of micrometers was observed (FIG. 1, right). In addition, the gel produced with HFIP and subjected to crosslinking with transglutaminase and water swelling was transparent. On the other hand, in the case of the gel produced with water-ethanol, many precipitates were observed (FIG. 2). The above results demonstrated that paclitaxel can be contained in gelatin in a finely-dispersed state by dissolving paclitaxel and gelatin in HFIP, followed by drying.

Example 3

A paclitaxel-containing albumin film and a paclitaxel-containing casein film were produced in the same manner as in Example 1 except that gelatin used in Example 1 was replaced by albumin (produced by Aldlich) and casein (produced by Wako Pure Chemical Industries, Ltd.), respectively. Observation was carried out in the same manner as in Example 2. As a result, no precipitation of paclitaxel was observed. These result demonstrated that a poorly water-soluble drug can be contained in gelatin, casein, and albumin in a finely-dispersed state.

Example 4

Drug-containing gelatin films were produced in the same manner as in Example 1 except that paclitaxel used in Example 1 was replaced by drugs with concentrations listed in Table 1 below. Observation was carried out in the same manner as in Example 2. The results demonstrated that a variety of poorly water-soluble drugs can be contained in the films at high concentrations according to the present invention.

[Table 1]

TABLE 1

| Drug | ClogP | Solubility in HFIP (mg/ml) | Drug/gelatin mass proportion (%) | | |
|---|---|---|---|---|---|
| | | | 0.1 | 1.0 | 5.0 |
| Paclitaxel | 4.7 | 200-500 | ○ | ○ (Example 1) | ○ |
| Aspirin | 1.0 | 200-500 | ○ | ○ | ○ |
| Phenytoin | 2.1 | 50-100 | ○ | ○ | Precipitated |
| Coumarin 1 | 3.6 | 200-500 | ○ | ○ | ○ |
| Coumarin 6 | 5.4 | 30-50 | ○ | Precipitated | Precipitated |
| Methyl yellow | 4.5 | 50-100 | ○ | ○ | Precipitated |
| Vitamin D3 | 9.4 | 200-500 | ○ | ○ | ○ |
| Rapamycin | 7.0 | 200-500 | ○ | ○ | ○ |
| Docetaxel | 4.2 | 100-200 | ○ | ○ | ○ |
| Camphorquinone | 1.5 | 200-500 | ○ | ○ | ○ |

(○: contained in a finely-dispersed state; Δ: partially precipitated)

Regarding the solubility in HFIP, HFIP samples at concentrations of 30, 50, 100, 200, and 500 mg/ml were prepared and the solubility of each drug was represented by a combination of "upper dissolution limit" and "lower precipitation limit" ("upper dissolution limit"–"lower precipitation limit") in accordance with the method described in the above paragraph 0026.

Example 5

The gelatin used in Example 1 was replaced by albumin or casein. Phenyloin or vitamin D3 was used as a poorly water-soluble compound. A phenyloin-containing albumin film, a phenyloin-containing casein film, a vitamin D3-containing albumin film, and a vitamin D3-containing casein film were produced. Observation was carried out in the same manner as in Example 2. In each case, no precipitation of the poorly water-soluble drug was observed.

Example 6

The film obtained in Example 1 was allowed to stand in a 0.8% transglutaminase (Activa TG-S produced by Ajinomoto Co., Inc.) aqueous solution at 25° C. for 17 hours. The thus obtained film was not dissolved in water at 37° C. even when immersed therein. Thus, production of a paclitaxel-containing crosslinked gelatin gel was achieved.

INDUSTRIAL APPLICABILITY

In the composition of the present invention, a poorly water-soluble compound is contained in a hydrophilic matrix in a finely-dispersed state, which is advantageous for control of the amount of such a poorly water-soluble compound (e.g., a drug) to be released, the release rate, and the drug efficacy. Further, when the composition of the present invention is used as a transdermally absorbable agent, transdermal absorption efficiency can be improved, which is also advantageous.

BRIEF DESCRIPTION OF THE DRAWINGS

FIG. 1 shows stereo microscopic images of paclitaxel-containing gelatin films. paclitaxel concentration upon casting: 1 mg/mL; gelatin concentration upon casting: 10%; paclitaxel-free gelatin film (left), paclitaxel-containing gelatin film produced with HFIP (center), and paclitaxel-containing gelatin film produced with water-ethanol (3:1) (right).

FIG. 2 shows stereo microscopic images of paclitaxel-containing crosslinked gelatin films. paclitaxel concentration upon casting: 1 mg/mL; gelatin concentration upon casting: 10%; casting solvent: HFIP (left), and water-ethanol (3:1) (right).

The invention claimed is:

1. A method for producing a composition wherein a poorly water-soluble compound is contained in a hydrophilic matrix in a finely-dispersed state, which consists of a step of coating and drying a mixture consisting of a poorly water-soluble compound, a hydrophilic matrix and an organic fluorine compound, that is prepared by dissolving a poorly water-soluble compound and a hydrophilic matrix in an organic fluorine compound, wherein the hydrophilic matrix consists of a protein.

2. The method of claim 1, wherein the poorly water-soluble compound is a drug.

3. The method of claim 1, wherein the hydrophilic matrix is a biopolymer.

4. The method of claim 1, wherein the protein is at least one selected from the group consisting of collagen, gelatin, albumin, casein, fibroin, fibrin, laminin, fibronectin, and vitronectin.

5. The method of claim 1, wherein the protein is albumin, casein, or gelatin.

6. The method of claim 1, wherein the hydrophilic matrix is crosslinked by heat or light, or with a crosslinking agent.

7. The method of claim 6, wherein the crosslinking agent is an enzyme.

8. The method of claim 7, wherein the enzyme is transglutaminase.

9. The method of claim 1, wherein the organic fluorine compound is a compound having a carbon number of 2 to 8.

10. The method of claim 1, wherein the organic fluorine compound is a compound having a carbon number of 2 or 3.

11. The method of claim 1, wherein the organic fluorine compound is 1,1,1-3,3,3-hexafluoro-2-propanol, 2,2,2-trifluoro ethanol, trifluoroacetic acid, or pentafluoro propionic acid.

12. The method of claim 1, wherein the poorly water-soluble compound has a log P (logarithm of 1-octanol/water partition coefficient) of 1 to 20.

13. The method of claim 1, wherein the poorly water-soluble compound has a log P (logarithm of 1-octanol/water partition coefficient) of 2 to 10.

14. The method of claim 2, wherein the drug is an anticancer agent, an immunosuppressive agent, an antiallergic agent, an antioxidant, an antithrombotic agent, an anti-inflammatory agent, a cosmetic component, or a supplement component.

15. The method of claim 2, wherein the drug is an anticancer agent or an immunosuppressive agent.

16. The method of claim 2, wherein the drug is paclitaxel or sirolimus.

17. The method of claim 1, wherein the mixture is coated on a substrate and is dried so that a film is formed.

18. The method of claim 1, wherein the thickness of the composition is 0.1 μm to 1 mm.

19. The method of claim 1, wherein the proportion of the poorly water-soluble compound in the hydrophilic matrix is 0.1% to 5%.

* * * * *